(12) United States Patent
Garvin et al.

(10) Patent No.: US 9,709,458 B1
(45) Date of Patent: Jul. 18, 2017

(54) SENSOR FOR DETECTING HYDROCARBON IN A STATIC DRAIN LINE

(71) Applicants: Elizabeth D Garvin, Jupiter, FL (US); Timothy J Miller, Jupiter, FL (US); Alex Pinera, Jupiter, FL (US)

(72) Inventors: Elizabeth D Garvin, Jupiter, FL (US); Timothy J Miller, Jupiter, FL (US); Alex Pinera, Jupiter, FL (US)

(73) Assignee: Florida Turbine Technologies, Inc., Jupiter, FL (US)

( * ) Notice: Subject to any disclaimer, the term of this patent is extended or adjusted under 35 U.S.C. 154(b) by 266 days.

(21) Appl. No.: 14/623,007

(22) Filed: Feb. 16, 2015

Related U.S. Application Data

(60) Provisional application No. 61/955,679, filed on Mar. 19, 2014.

(51) Int. Cl.
*G01M 3/38* (2006.01)
*G01J 3/50* (2006.01)
*G01M 3/04* (2006.01)
*F02K 9/00* (2006.01)

(52) U.S. Cl.
CPC ............. *G01M 3/38* (2013.01); *F02K 9/00* (2013.01); *G01J 3/50* (2013.01); *G01M 3/042* (2013.01)

(58) Field of Classification Search
CPC ........................................................ G01M 3/38
See application file for complete search history.

(56) References Cited

U.S. PATENT DOCUMENTS

| | | | |
|---|---|---|---|
| 7,687,270 B1 * | 3/2010 | Crispin | G01M 3/042 422/400 |
| 8,057,165 B1 | 11/2011 | Garvin et al. | |
| 8,845,274 B1 | 9/2014 | Garvin et al. | |
| 2012/0210980 A1 * | 8/2012 | Bedekar | F02M 55/004 123/456 |

* cited by examiner

*Primary Examiner* — Hezron E Williams
*Assistant Examiner* — Timothy Graves
*(74) Attorney, Agent, or Firm* — John Ryznic

(57) ABSTRACT

A hydrocarbon leak detection sensor having a hydrocarbon indicator paint applied to a surface exposed to a flow in which the presence of a hydrocarbon is detected. The sensor is located at a low point in a static drain line that is connected to a main fuel line of a liquid propellant rocket engine between a main fuel valve and a fuel injector of a combustion chamber. The sensor includes a housing with a flow inlet port and a flow outlet port with an optical device opposed to a removable plug that secures a target disk with a hydrocarbon indicator paint applied to an exposed surface. A light source is used to illuminate the hydrocarbon indicator that changes color from white to red in the presence of a hydrocarbon.

15 Claims, 6 Drawing Sheets

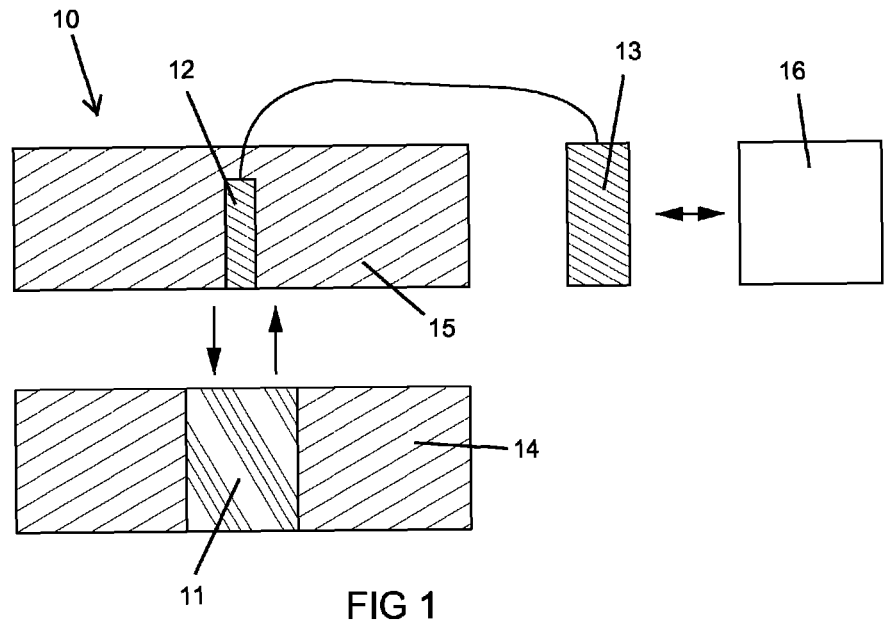
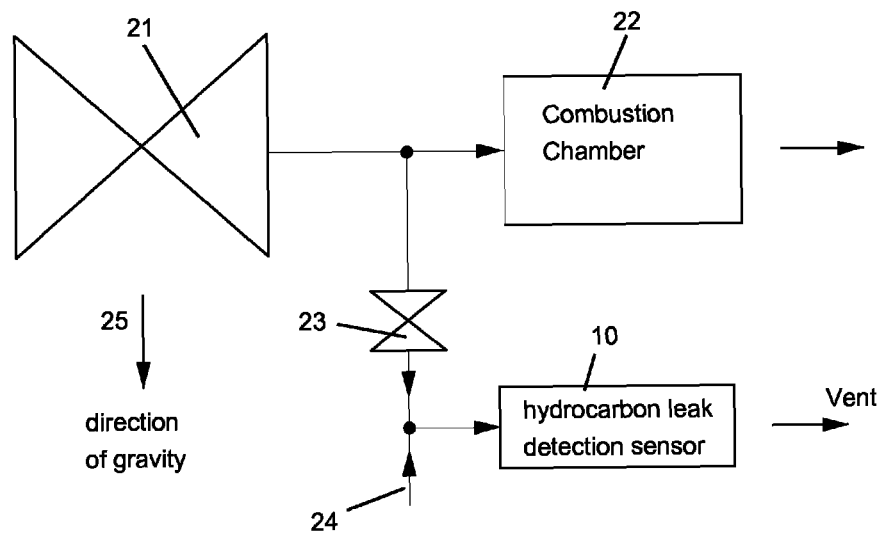

SENSOR FOR DETECTING HYDROCARBON IN A STATIC DRAIN LINE

CROSS-REFERENCE TO RELATED APPLICATIONS

This application claims the benefit to U.S. Provisional Application 61/955,679 filed Mar. 19, 2014 and entitled SENSOR FOR DETECTING HYDROCARBON IN A STATIC DRAIN LINE.

GOVERNMENT LICENSE RIGHTS

None.

BACKGROUND OF THE INVENTION

Field of the Invention

The present invention relates generally to a rocket engine, and more specifically to a sensor for detecting a hydrocarbon leakage of a main engine fuel valve in a rocket engine. The sensor can also be used in the oil and gas, aircraft, automotive, and marine industries, where the detection of unintentional hydrocarbon fuel leakage is desired.

Description of the Related Art Including Information Disclosed Under 37 CFR 1.97 and 1.98

In a rocket engine turbopump, an inter-propellant seal (IPS) is necessary to separate the fuel from the oxidizer. If the two should mix inside the turbopump, they may likely ignite and cause a catastrophic engine failure. Depending on the engine cycle and turbopump configuration, the IPS may be required to separate the fuel rich turbine from the oxidizer pump, such as on the SSME (space shuttle main engine). For a single shaft turbopump, the IPS separates the fuel and the oxidizer pumps.

In a typical IPS used in a turbopump of a liquid propellant rocket engine, there are generally at least three discrete seal components. An inert gas, such as helium or nitrogen, is used to provide a buffer or barrier zone between the two propellants. In addition to the seals themselves, the two sources, the two drains and the buffer gas supply require equal attention in design. During operation, the buffer cavity pressure is always maintained higher than either of the adjacent drain pressures in order that the two volatile fluids do not mix. However, in the event that the fluids do mix, the turbopump should be shut down immediately. Currently, the prior art does not have any process involved to determine if the fuel is mixing with the oxidizer in the inter-propellant seal.

A re-usable engine whose fuel is rocket propellant (RP), a higher grade version of kerosene, presents a unique ground support requirement. After the engine has been run once, what is typically done is to maintain the buffer purge flow continuously for 24 hours 7 days per week. This is done because all of the leftover kerosene residue cannot be removed from the pump, and over time this residue may wick between the seals over the oxidizer drain cavity and even to the oxidizer side of the pump. Wicking is when the fluid slowly flows along the surface while sticking to the surface. If one chooses not to continuously run the buffer purge flow, one runs the risk of kerosene wicking to the oxidizer side of the pump and causing a catastrophic failure upon the next use of the engine.

What is currently done is to run the buffer purge flow continuously in-between uses of the engine. If the ground support requirement of continuous buffer purge flow cannot be met, another option is to place some type of a hydrocarbon detection sensor in the oxidizer drain cavity. During the pre-flight checklist, when the purge flow is started the hydrocarbon sensor would detect whether or not kerosene has wicked over to the oxidizer drain cavity. If this has happened, it would require an engine tear-down to clean all the areas of the turbopump where the oxidizer flows.

In a liquid propellant rocket engine, a main fuel valve supplies liquid fuel to a combustion chamber through an injector. If fuel were to leak beyond the main fuel valve prior to engine operation, the fuel could ignite with the oxidizer prior to the intended ignition, causing destruction of the engine

BRIEF SUMMARY OF THE INVENTION

A hydrocarbon indicator changes color when exposed to hydrocarbon fuel. The surface of the hydrocarbon indicator is illuminated by a light source, allowing an optical sensor to view the color change and send signals to a data processor. The data processor includes algorithms to detect the color change and send an alert that hydrocarbon is present.

A hydrocarbon leak detection sensor uses the hydrocarbon indicator in a sensor that is located in a low point of a static drain line connected to a main fuel line between a main fuel valve and an injector and combustion chamber of a liquid propellant rocket engine. The hydrocarbon leak detection sensor is connected to a vent and will detect the presence of a hydrocarbon downstream from the engine's primary fuel valve.

The hydrocarbon leak detection sensor includes a optical device port and a light source port with a removable plug that pinches a replaceable target disk that has on it the hydrocarbon indicator applied on an exposed surface. A flow inlet port and a flow outlet port is connected to the sensor housing to pass fluid from the drain line through the sensor. A light source illuminates the hydrocarbon indicator and the optical device senses a change of color of the hydrocarbon indicator when a hydrocarbon is present.

In another embodiment, the hydrocarbon indicator is applied to a target disk having holes therein so that the fluid can pass through. In another embodiment, the hydrocarbon indicator is applied directly to a surface of the fluid passage. In another embodiment, the hydrocarbon indicator is applied to a plate with thin wires connecting it to a housing that carries the optical device with the light source. In another embodiment, the hydrocarbon indicator is applied onto a screen that will allow passage of the fluid. In another embodiment, the hydrocarbon indicator is applied onto a conical shaped set screw inserted into a bushing.

BRIEF DESCRIPTION OF THE SEVERAL VIEWS OF THE DRAWINGS

FIG. 1 shows a schematic view of the function of the hydrocarbon leak detection sensor of the present invention.

FIG. 2 shows a schematic view of a hydrocarbon leak detection sensor in a drain line downstream from a main fuel valve of the present invention.

DETAILED DESCRIPTION OF THE INVENTION

Figure 3:
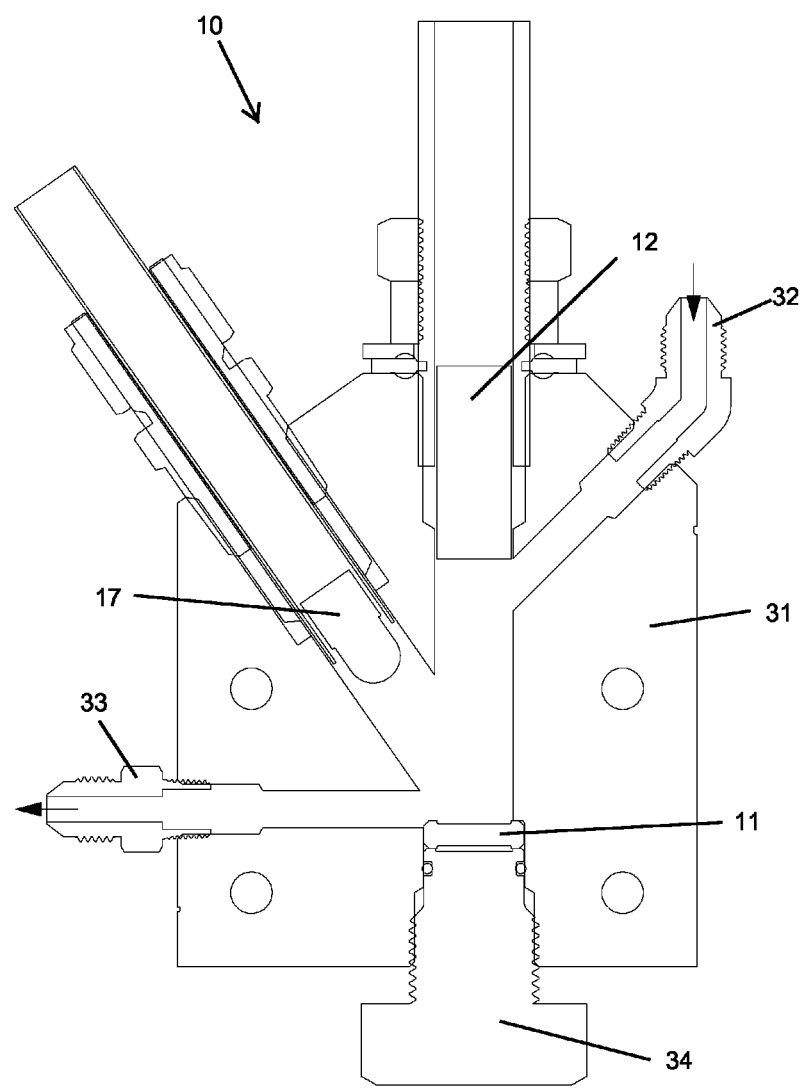
FIG. 3 shows a schematic view of a hydrocarbon leak detection sensor of a first embodiment of the present invention.

The present invention is a sensor that detects the presence of hydrocarbon fuel and signals that the detection has occurred. The sensor includes a hydrocarbon indicator and an optical device with a data processor. The hydrocarbon indicator changes color from white to red when in contact with hydrocarbon. The optical device includes a light source to illuminate the surface of the color change. The optical device views the color change and interprets it as signals sent to the data processor. The data processor includes algorithms to determine when an alert is required. The sensor is packaged for use in a static tube or drain line. The sensor housing contains multiple ports used to hold and secure the optical device, light source, and hydrocarbon indicator at optimum distances from each other. The sensor housing also has inlet and outlet ports to allow the flow from the tube or drain line to pass through the sensor unobstructed. The hydrocarbon indicator is applied on easily removable and replaceable targets to allow the sensor to be reusable.

The problem solved by the hydrocarbon leak detection sensor of the present invention is the detection of unintentional hydrocarbon fuel leakage. The sensor replaces the need for manually checking for hydrocarbon leaks in static drain lines; therefore, the sensor will improve safety and reduce maintenance time and labor. One use for the sensor is to detect leakage from the primary main engine fuel valve upstream of an injector in a rocket engine. If fuel were to leak beyond the main fuel valve prior to engine operation, the fuel could ignite with the oxidizer prior to the intended ignition, causing destruction of the engine. The hydrocarbon leak detection sensor would be able to detect the fuel leakage and signal to the engine health management system that a leak has occurred, so the engine can be cleaned and inspected before operation.

By locating the sensor in a low point static drain line, the sensor will not be in the direct flow path of the fuel line and therefore will not be exposed to engine conditions or interrupt engine operation. Instead, any fuel that leaks past the primary fuel valve will enter the drain line, which is positioned at the bottom of the main line to be aligned with gravity. Other industries where this invention could be used include oil and gas, aircraft, automobile, and marine industries.

The function of the hydrocarbon leak detection sensor is shown in FIG. 1. The sensor 10 includes a hydrocarbon indicator 11 and an optical 12 device with a data processor 13. The hydrocarbon indicator 11 can be on a rotating shaft or a stationary component. in the FIG. 1 embodiment, the optical device 12 is on a stationary housing 15 while the hydrocarbon indicator 11 can be on a rotating shaft or a stationary component 14. The hydrocarbon indicator 11 changes color from white to red when in contact with hydrocarbon. A white light source from the optical device illuminates the surface and a color reading is reflected back from the hydrocarbon indicator to the optical device 12 (as represented by the two arrows). The optical device 12 includes a light source (such as a white light source) to illuminate the surface of the color change. The optical device 12 views the color change and interprets it as signals sent to the data processor. The data processor includes algorithms to determine when an alert 16 is required.

FIG. 2 shows the hydrocarbon leak detection sensor 10 in a low point drain line downstream from an engine's primary fuel valve. A main fuel valve 21 is located in a main fuel line flowing into a combustion chamber 22 with a fuel injector. A low point static drain line with an isolation valve 23 is connected to the main fuel line. The hydrocarbon leak detection sensor 10 is off of this drain line and is vented to atmosphere. A gaseous nitrogen purge line 24 is connected to the drain line between the isolation valve 23 and the sensor 10. A direction of gravity is represented by the arrow 25.

FIG. 3 shows the first embodiment of the hydrocarbon leak detection sensor 10 in a static drain line. The sensor uses a custom-designed housing 31 that can be manufactured using conventional machining. The housing 31 includes a flow inlet port 32 and a flow outlet port 33 to attach to the static drain line tubing, to allow the flow to pass through the sensor unobstructed. The housing 31 also includes ports to hold and secure the optical device 12, light source 17, and hydrocarbon indicator 11. The optical device 12 is placed opposite the hydrocarbon indicator 11 with direct line-of-sight, whereas the light source 17 is set off at an angle. The hydrocarbon indicator 11 is applied to a small removable disk, called the target. The target is replaceable so the sensor can be reused. The target is held in place by a removable plug 34. In FIG. 3, the direction of gravity is downward. In one embodiment, the hydrocarbon indicator is placed on a removable target disk, and the removable plug is screwed into the housing to pinch the target disk between the housing and the plug. This design allows for the hydrocarbon indicator to be replaced by simply removing the plug 34 and dropping out from the housing the target disk with the hydrocarbon indicator thereon. To replace the hydrocarbon indicator, only the target disk must be removed and replaced. The plug 34 can be reused.

Figure 4:
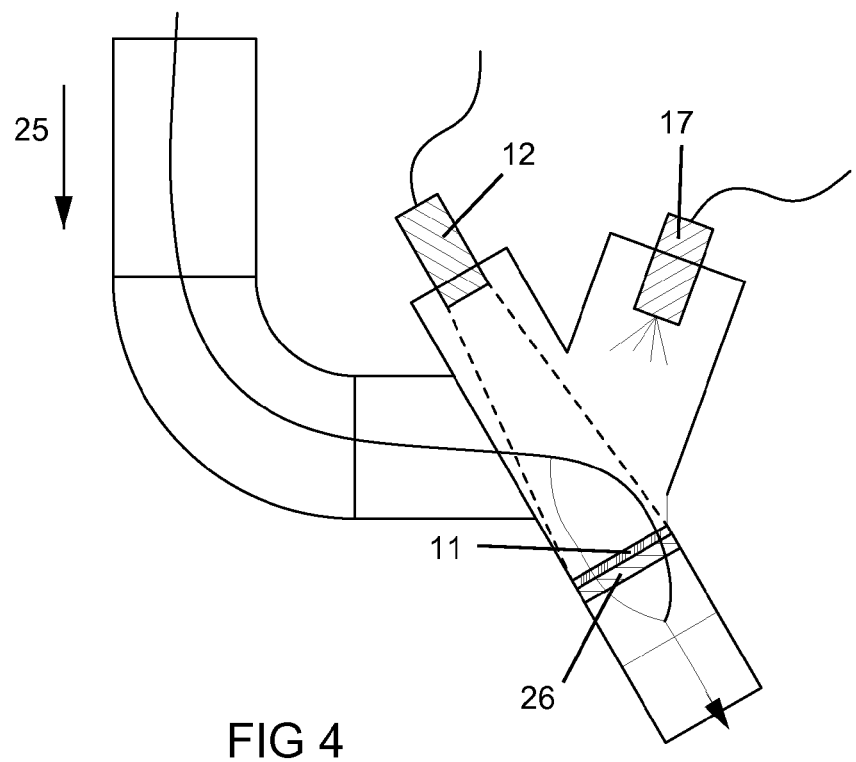
FIG. 4 shows a schematic view of a hydrocarbon leak detection sensor of a second embodiment of the present invention.

FIG. 4 shows the second embodiment of the hydrocarbon leak detection sensor in a static drain line. The sensor uses a custom-designed housing that can be manufactured using additive manufacturing (3D printing). The housing includes ports for the optical device 12, light source 17, and hydrocarbon indicator 11. The optical device 12 is placed opposite the hydrocarbon indicator 11 with direct line-of-sight, whereas the light source 17 is set off at an angle. The hydrocarbon indicator is applied to a small removable disk (target) 26 which has holes in it to allow the flow to pass through the disk 26. The target is replaceable so the sensor can be reused. The housing includes flow inlet and outlet ports to attach to the static drain line tubing, and the outlet port is also used to hold the removable target.

FIGS. 5-11 show seven additional embodiments of the hydrocarbon leak detection sensor in a static drain line. Each of these embodiments utilizes off-the-shelf tube fittings to house the sensor and connect it to the drain line tubing. Each of these embodiments uses an optical device with a built-in light source.

Figure 5:
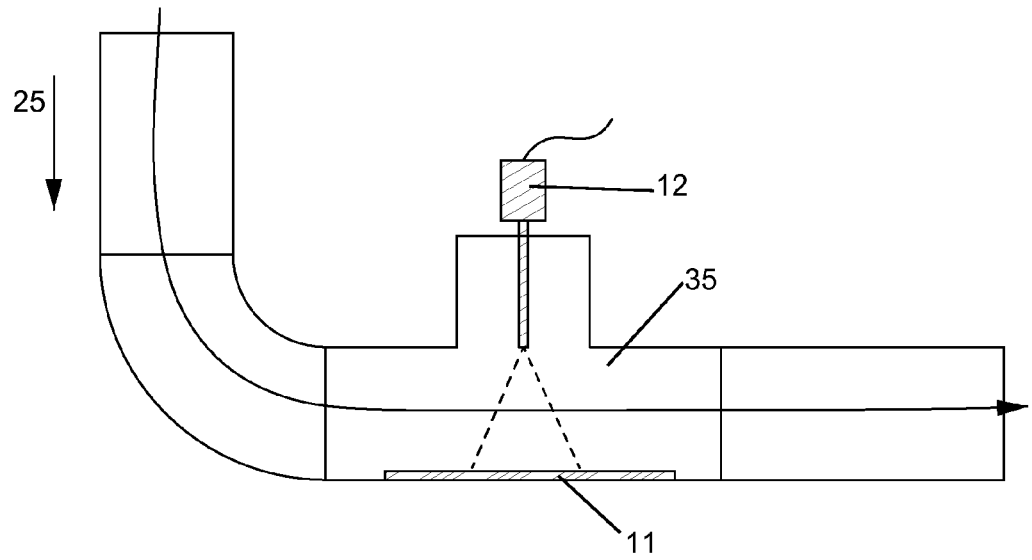
FIG. 5 shows a schematic view of a hydrocarbon leak detection sensor of a third embodiment of the present invention.

The third embodiment of the sensor is shown in FIG. 5 and includes an optical device connected through a Tee fitting 35 in the drain flow path. A hydrocarbon indicator 11 is applied directly to the Tee fitting 35 opposite to the optical device 12.

Figure 6:
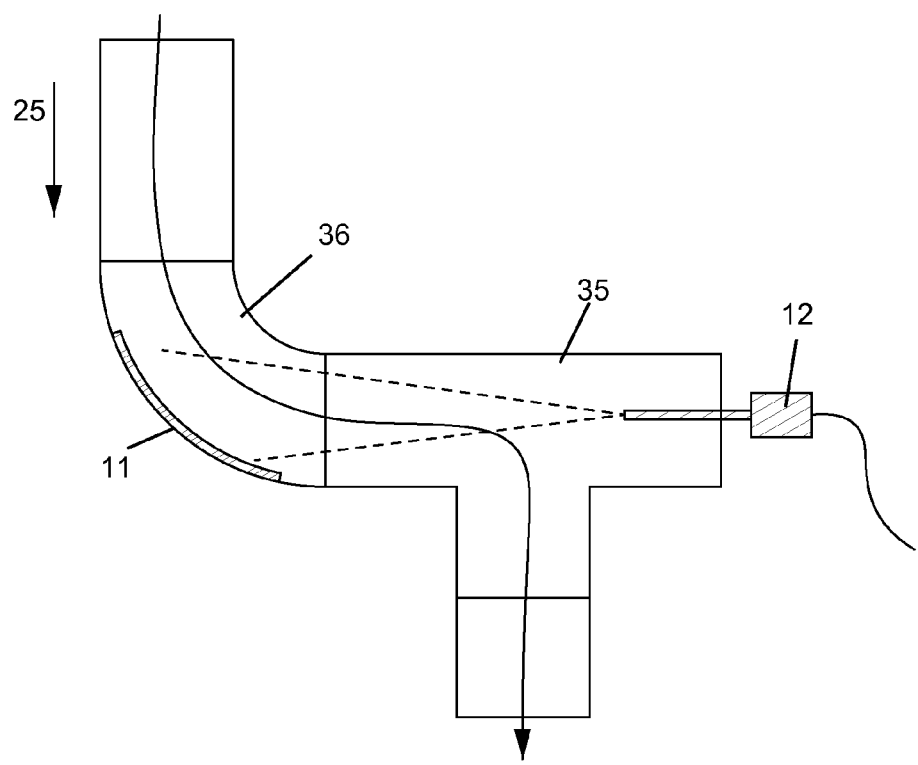
FIG. 6 shows a schematic view of a hydrocarbon leak detection sensor of a fourth embodiment of the present invention.

FIG. 6 shows a fourth embodiment of the sensor with a Tee fitting 35 having an optical device 12 connected at one end and a hydrocarbon indicator 11 applied to a curved surface on an elbow fitting 36 in the drain flow path.

Figure 7:
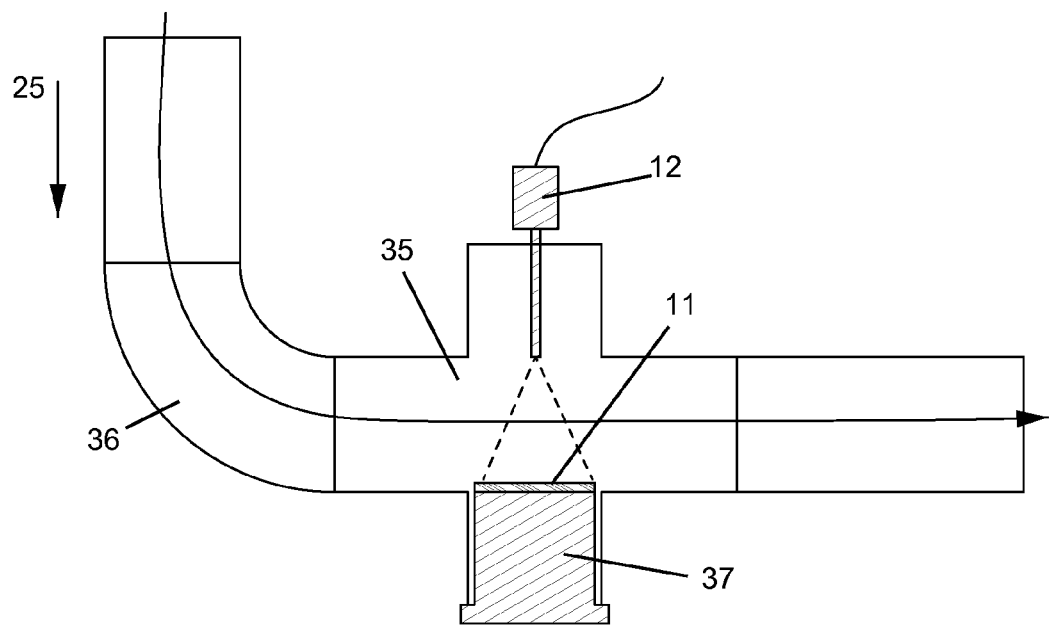
FIG. 7 shows a schematic view of a hydrocarbon leak detection sensor of a fifth embodiment of the present invention.

FIG. 7 shows a fifth embodiment of the sensor with an optical 12 device connected through one end of a cross connector. A removable cap 37 with a hydrocarbon indicator 11 applied inside is used on an opposite side of the cross connector from an optical device 12.

Figure 8:
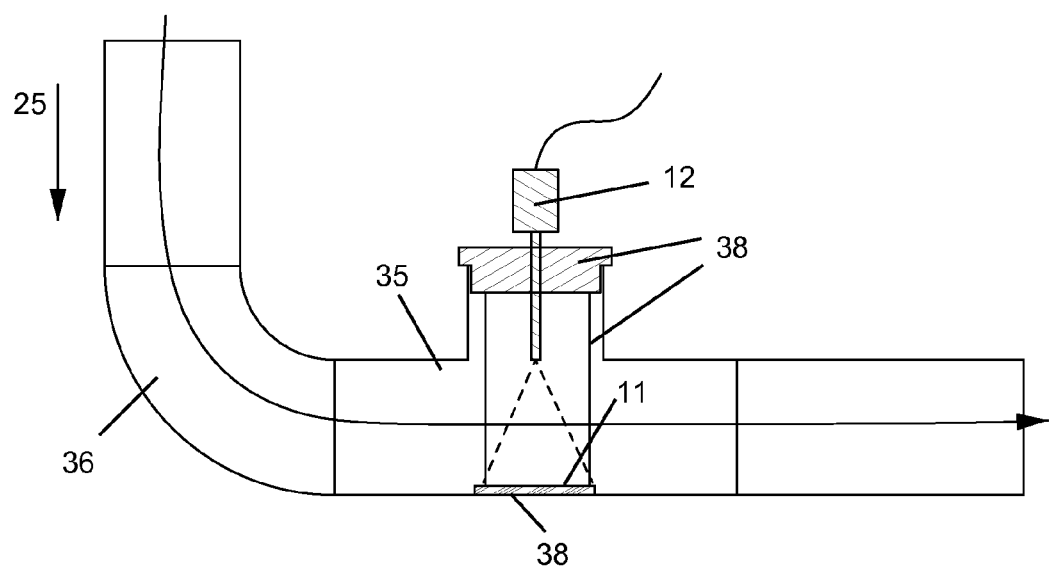
FIG. 8 shows a schematic view of a hydrocarbon leak detection sensor of a sixth embodiment of the present invention.

FIG. 8 shows a sixth embodiment of the sensor with a Tee fitting 35 having a removable housing 38 that contains both an optical device 12 and a hydrocarbon indicator 11 that is applied to a plate 38 with thin wires connecting it to the removable housing.

Figure 9:
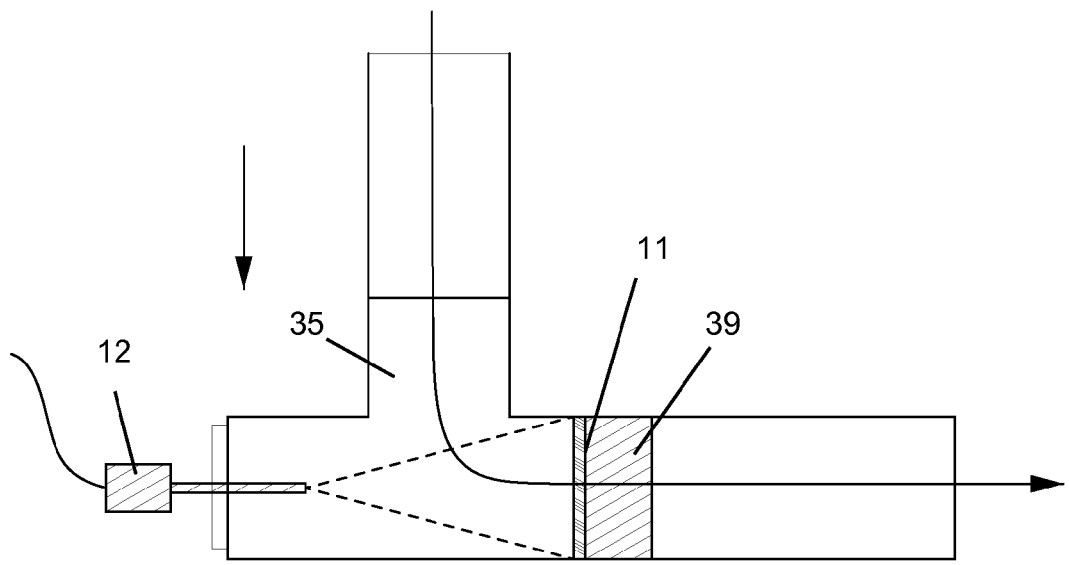
FIG. 9 shows a schematic view of a hydrocarbon leak detection sensor of a seventh embodiment of the present invention.

FIG. 9 shows a seventh embodiment of the sensor with a Tee fitting 35 having an optical device 12 connected through one end and a screen 39 with a hydrocarbon indicator 11 applied to the screen 39 connected on an opposite side of the Tee fitting 35. The flow passes through the screen 39.

Figure 10:
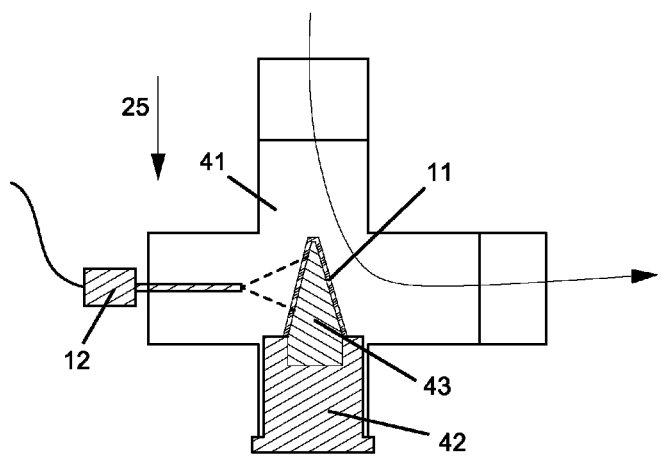
FIG. 10 shows a schematic view of a hydrocarbon leak detection sensor of an eighth embodiment of the present invention.

FIG. 10 shows an eighth embodiment of the sensor with a cross connector 41 having an optical device 12 connected though one end. A bushing 42 holding a set screw 43 with tapered threads is connected through an end of the cross connector 41 that is perpendicular to an optical device 12. A hydrocarbon indicator 11 is applied to the threads of the set screw.

Figure 11:
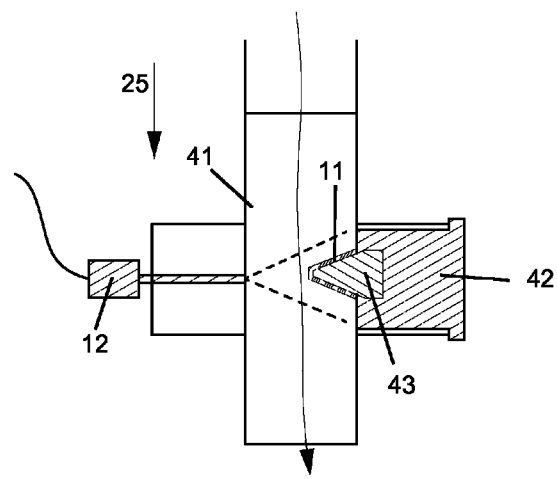
FIG. 11 shows a schematic view of a hydrocarbon leak detection sensor of a ninth embodiment of the present invention.

FIG. 11 shows a ninth embodiment of the sensor with a cross connector 41 having an optical device 12 connected though one end. A bushing 42 holding a set screw 43 with tapered threads is connected through an end of the cross connector 41 that is opposite to an optical device 12. A hydrocarbon indicator 11 is applied to the threads of the set screw 43.

The hydrocarbon indicator used for all embodiments is the PinPoint Colorimetric Developer ODP-110 by the American Gas and Chemical Co. Ltd. The product is in a paint form that can be applied as a coating and the paint changes color from white to red when a hydrocarbon such as fuel or oil is in contact with the paint. There is also similar powder spray and aerosol spray products by this same company. To improve how well the paint product adheres to surfaces, the paint was mixed with fiber glass.

The optical device and data processor can be any kind of spectrometer or color sensor. The device could use a fiber optic probe to minimize the size of the optical device within the housing. The first and second embodiments of the sensor use the ENV-RGB Color Detector Probe (part #SEN-202RGB) made by Atlas Scientific LLC. A miniature LED light bulb is used as the light source. Custom Arduino algorithm programming is used to interpret the signals from the Color Detector Probe and send an alert if hydrocarbon is detected.

We claim the following:
1. A liquid propellant rocket engine with a hydrocarbon leak detection sensor comprising:
   a main fuel valve;
   a combustion chamber of the rocket engine;
   a fuel injector discharging into the combustion chamber;
   a main fuel line connecting the main fuel valve to the fuel injector;
   a low static point drain line connected to the main fuel line between the main fuel valve and the fuel injector; and,
   a hydrocarbon leak detection sensor connected to the low static point drain line to detect a presence of a hydrocarbon in the main fuel line.
2. The liquid propellant rocket engine of claim 1, and further comprising:
   the hydrocarbon leak detection sensor includes a hydrocarbon indicator and an optical device with a light source both located opposite from the hydrocarbon indicator in a flow path.
3. The liquid propellant rocket engine of claim 2, and further comprising:
   the optical device and the light source are offset from one another at an angle.
4. The liquid propellant rocket engine of claim 3, and further comprising:
   the optical device is directly opposed to the hydrocarbon indicator while the light source is offset from the hydrocarbon indicator.
5. The liquid propellant rocket engine of claim 2, and further comprising:
   the optical device and the light source are formed as an integral piece.
6. The liquid propellant rocket engine of claim 2, and further comprising:
   the hydrocarbon indicator is formed on a surface having a plurality of holes to allow for passage of a flow within the flow path.
7. The liquid propellant rocket engine of claim 1, and further comprising: the hydrocarbon indicator is formed on a screen that allows for a flow to pass through.
8. The liquid propellant rocket engine of claim 1, and further comprising: the hydrocarbon indicator is part of a removable plug secured to a flow path of the hydrocarbon leak detection sensor.
9. The liquid propellant rocket engine of claim 8, and further comprising:
   the removable plug includes a cone-shaped member on which the hydrocarbon indicator is formed.
10. A hydrocarbon leak detection sensor to detect for the presence of a hydrocarbon is a gas flow, the hydrocarbon leak detection sensor comprising:
    a housing;
    an optical device port in the housing;
    a light source port in the housing;
    a plug port in the housing located opposite to the optical device port;
    a flow inlet port in the housing;
    a flow outlet port in the housing;
    an optical device secured in the optical device port;
    a light source secured in the light source port;
    a fluid flow path formed within the housing and connecting the flow inlet port to the flow outlet port;
    a removable plug secured within the plug port;
    a hydrocarbon indicator secured on the plug and facing the optical device; and,
    a static drain line tube connected to the flow inlet port; whereby,
    a fluid flow having a hydrocarbon present will flow from the static drain line tube and through the fluid flow path such that the hydrocarbon indicator will display a certain color that can be detected by the optical device.
11. The hydrocarbon leak detection sensor of claim 10, and further comprising:

the optical device port is located on a top end of the housing; and, the removable plug port is located on a bottom end of the housing.

12. The hydrocarbon leak detection sensor of claim 11, and further comprising:

the light source port is located in the housing offset from the optical device port.

13. The hydrocarbon leak detection sensor of claim 11, and further comprising:

the flow inlet port is located on an upper section of the housing adjacent to the optical device port; and, the flow outlet port is located on a lower section adjacent to the removable plug port.

14. The hydrocarbon leak detection sensor of claim 10, and further comprising:

the optical device and the light source both close off the ports to form a closed fluid passage from the flow inlet port to the flow outlet port within the housing.

15. The hydrocarbon leak detection sensor of claim 10, and further comprising:

the hydrocarbon indicator is coated on a target disk; and, the target disk is secured within the housing by the removable plug such that the hydrocarbon indicator can be replaced by replacing the target disk.

\* \* \* \* \*